United States Patent [19]

Hoelscher et al.

[11] Patent Number: 4,634,767

[45] Date of Patent: Jan. 6, 1987

[54] METHOD FOR PREPARING SPIRO(INDOLINE)-TYPE PHOTOCHROMIC COMPOUNDS

[75] Inventors: Charles H. Hoelscher, Doylestown; Douglas S. McBain, Norton, both of Ohio

[73] Assignee: PPG Industries, Inc., Pittsburgh, Pa.

[21] Appl. No.: 771,920

[22] Filed: Sep. 3, 1985

[51] Int. Cl.$^4$ .................. C07D 491/10; C07D 498/00; C07D 498/10

[52] U.S. Cl. .......................... 544/71; 546/15; 548/409

[58] Field of Search ........................ 544/71; 546/15; 548/409

[56] References Cited

U.S. PATENT DOCUMENTS

| 3,562,172 | 2/1971 | Ono et al. | 252/300 |
| 3,578,602 | 5/1971 | Ono et al. | 252/300 |
| 3,671,543 | 6/1972 | Koga et al. | 548/409 |
| 3,843,550 | 10/1974 | Hinnen | 252/300 |
| 3,950,356 | 4/1976 | Hinnen | 548/409 |
| 4,215,010 | 7/1980 | Hovey et al. | 252/300 |
| 4,342,668 | 8/1982 | Hovey et al. | 252/586 |

FOREIGN PATENT DOCUMENTS 141407 5/1985 European Pat. Off. .

Primary Examiner—Richard L. Raymond
Attorney, Agent, or Firm—Irwin M. Stein

[57] ABSTRACT

Spiro(indoline)-type photochromic compounds are prepared by admixing a solution of the Fischer's Base reactant in non-polar solvent with a mixture of the pyran- or oxazine-forming reactant, e.g., 5-nitroso-6-hydroxy quinoline, in polar solvent and heating the resulting reaction medium at temperatures sufficient to form the corresponding spiro(indoline)-type compound while simultaneously removing co-product water.

18 Claims, No Drawings

METHOD FOR PREPARING SPIRO(INDOLINE)-TYPE PHOTOCHROMIC COMPOUNDS

DESCRIPTION OF THE INVENTION

The present invention relates to an improved method for preparing spiro(indoline)-type photochromic compounds. Photochromism is a reversible phenomenon illustrated by a compound which, when exposed to the radiation of light such as sunlight or the light of a mercury lamp, changes color and then returns to its original color if the radiation is discontinued or the compound is stored in the dark. A compound illustrating this property is called a "photochromic compound".

Spiro(indoline)-type compounds have been described as possessing photochromic properties and have been suggested for use in applications in which a color change or darkening induced by sunlight is a desirable feature. For example, spiro(indoline) naphthoxazine compounds are described in U.S. Pat. Nos. 3,562,172, 3,578,602, 4,215,010, and 4,342,668. Spiro(indoline)-pyrido benzoxazines have been described in, for example, European Patent Publication No. 141 407.

The aforesaid spiro(indoline)-type compounds may be prepared by a condensation reaction of the corresponding Fischer's Base reactant with the corresponding 5-nitroso (or 5-formyl)-6-hydroxynaphthalene (or quinoline) reactant, the 5-nitroso compounds being referred to herein as the oxazine-forming reactant and the 5-formyl compounds being referred to herein as the pyran-forming reactant. The condensation reaction is typically conducted in a solvent such as ethanol. The Fischer's Base reactant may be formed in-situ by reaction of the corresponding indolium salt, e.g., the iodide salt, with a base such as triethylamine, thereby to form the free Fischer's Base and insoluble triethylammonium iodide.

The aforedescribed process for preparing spiro(indoline)-type oxazine compounds has several disadvantages including low yields of the photochromic product, formation of tarry by-products and incorporation of the insoluble salt, e.g., triethylammonium iodide, with the product photochromic compound.

It has now been discovered that the yield of photochromic compound can be significantly improved, formation of tarry by-products significantly reduced, and incorporation of the insoluble salt triethylammonium iodide in the product photochromic compound eliminated. Such improvements are obtained by incorporating the free Fischer's Base reactant in non-polar solvent and the oxazine-forming or pyran-forming reactant in polar solvent, the non-polar and polar solvents being miscible, and charging the resulting liquid media into a reaction vessel, thereby to form a liquid reaction medium. The reaction medium is heated to temperatures sufficient to form the product photochromic compound and remove co-product water, usually by azeotropic distillation with the polar solvent. The azeotrope may also be a three component mixture of water, polar solvent and non-polar solvent.

DETAILED DESCRIPTION OF THE INVENTION

The process of the present invention may be used to prepare spiro(indoline)-type photochromic compounds. In particular, it is contemplated that the process may be used to prepare spiro(indoline) pyrido benzoxazines, spiro(indoline) naphthoxazines, spiro(indoline) naphthopyrans, and spiro(indoline) quinopyrans. The aforesaid spiro(indoline)-type photochromic compounds may be represented by the following graphic formula:

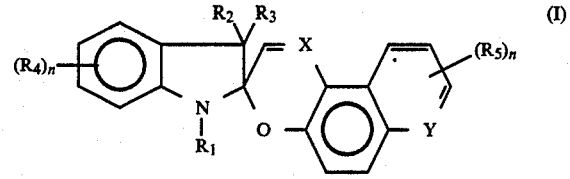

wherein X and Y are each selected from the group consisting of carbon and nitrogen, and the letter n is the integer 0, 1 or 2. In graphic formula I, $R_1$–$R_5$ represent substituent groups typically associated with those spiro-(indoline)-type compounds known to those skilled in the art. The nature of the substituents is not deemed critical to the essence of the method described herein since the substituents on the reactants should not affect the condensation reaction of the Fischer's Base and oxazine- or pyran-forming reactants.

In the above graphic formula I, $R_1$ may be selected from the group consisting of hydrogen, $C_1$–$C_8$ alkyl, e.g., methyl, ethyl, propyl, and butyl, etc., phenyl, phen($C_1$–$C_4$) alkyl, allyl, and mono- and di- substituted phenyl, said phenyl substituents being selected from $C_1$–$C_4$ alkyl and $C_1$–$C_5$ alkoxy, e.g., methoxy, ethoxy, propoxy, butoxy, and pentoxy. Preferably, $R_1$ is hydrogen, $C_1$–$C_4$ alkyl, phenyl or the benzyl radical.

$R_2$ and $R_3$ of graphic formula I may each be selected from the group consisting of hydrogen, $C_1$–$C_5$ alkyl, phenyl, mono- and di-substituted phenyl, benzyl or combine to form a cyclic ring selected from the group consisting of an alicyclic ring containing from 6 to 8 carbon atoms (including the spiro carbon atom), norbornyl and adamantyl. The phenyl substitutents may be selected from $C_1$–$C_4$ alkyl and $C_1$–$C_5$ alkoxy radicals. Preferably, $R_2$ and $R_3$ are each selected from $C_1$–$C_5$ alkyl, such as methyl and ethyl. When one of $R_2$ or $R_3$ is a tertiary alkyl radical, such as tertiary butyl or tertiary amyl, the other is preferably an alkyl radical other than a tertiary alkyl radical.

$R_4$ in graphic formula I may be selected from the group consisting of $C_1$–$C_5$ alkyl, halogen, $C_1$–$C_5$ alkoxy, nitro, cyano, $C_1$–$C_4$ haloalkyl and $C_1$–$C_4$ polyhaloalkyl, and $C_1$–$C_8$ alkoxycarbonyl. When n is 0, $R_4$ is hydrogen. The substituent(s) $R_4$ may be present on any of the available carbon atoms of the indolino portion of the compound, i.e., on the 4, 5, 6, or 7 positions. When n is 2, it is preferable that the substituents be present at the 4 and 5, 5 and 6, 4 and 7, or 6 and 7 positions. While any halogen, i.e., chlorine, bromine, iodine and fluorine, may be used in respect to the halogen or haloalkyl substituents, chlorine, bromine and trifluoromethyl are preferred. Preferably, $R_4$ is selected from the group consisting of $C_1$–$C_2$ alkyl, e.g., methyl and ethyl, chlorine, bromine, and $C_1$–$C_5$ alkoxy, e.g., methoxy and ethoxy, when n is 1 or 2.

$R_5$ in graphic formula I may be selected from halogen, e.g., chlorine and bromine, and $C_1$–$C_4$ alkoxy, e.g., methoxy. When n is 0, $R_5$ is hydrogen.

Of particular interest, are compounds represented by graphic formula I wherein $R_1$ is a $C_1$–$C_4$ alkyl, such as methyl, ethyl, n-propyl, isopropyl, n-butyl, secondary butyl, isobutyl and tertiary butyl; $R_2$ and $R_3$ are each methyl, ethyl, or phenyl; $R_4$ is hydrogen, methyl, methoxy, or chloro; $R_5$ is hydrogen or $C_1-C_4$ alkoxy; and n is 0, 1 or 2.

The method of the present invention is particularly useful for the preparation of spiro(indoline)-type photochromic compounds represented by graphic formulae II and III.

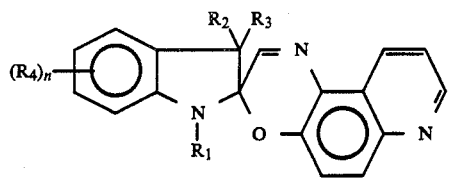

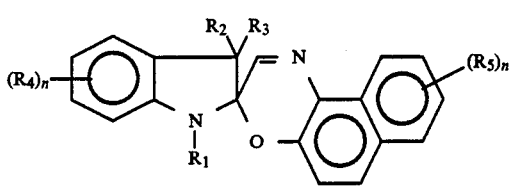

wherein $R_1$, $R_2$, $R_3$, $R_4$, $R_5$ and n are as hereinabove defined.

The above-described spiro(indoline)-type compounds can be prepared by condensation of a free Fischer's Base represented by graphic formula IV

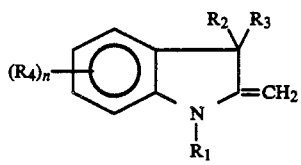

wherein $R_1$, $R_2$, $R_3$, and $R_4$ are as defined hereinabove, with a polycyclic second reactant represented by graphic formula V,

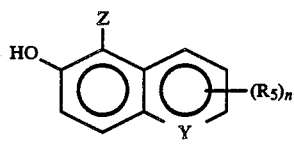

wherein Y, $R_5$ and n are as defined hereinabove, and Z is nitroso or formyl. The compounds represented by graphic formula V are 5-nitroso (or formyl) -6-hydroxy naphthalene (or quinoline) compounds, which may be represented graphically by formulae VI–IX.

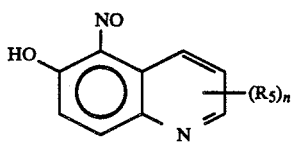

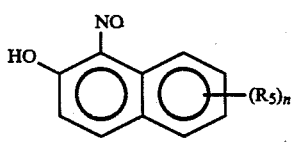

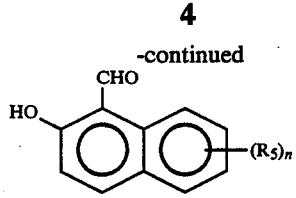

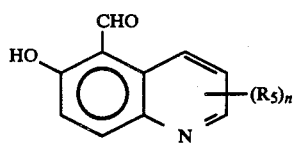

wherein $R_5$ and n are as defined hereinabove.

The free Fischer's Base may be preformed or formed in situ by utilizing the corresponding indolium salt, e.g., the iodide salt, and a basic reagent, such as triethylamine. The triethylammonium hydrohalide, e.g, hydroiodide, salt which is formed in-situ remains in solution with the Fischer's Base. Separation of the triethylammonium hydrohalide salt from the reaction product can be accomplished by selectively dissolving the photochromic compound in a hydrocarbon solvent, such as toluene, followed by filtration to remove the hydrohalide salt. The hydrocarbon solvent can then be removed by distillation, e.g., vaccum distillation, to recover the photochromic compound.

In accordance with an embodiment of the present invention, the Fischer's Base reactant is pre-formed by contacting the indolium salt with an alkaline aqueous medium and extracting the resulting free Fischer's Base in an inert, liquid non-polar organic solvent. The aforesaid preparation may be performed by adding the indolium salt to a reaction vessel containing the alkaline aqueous medium and the non-polar organic solvent. Vigorous stirring of the mixture results in extraction of the free Fischer's Base reactant into the organic phase which is then separated from the aqueous phase. The aqueous phase can be extracted further with additional organic solvent and this material added to the separated organic phase for subsequent use in preparing the spiro-(indoline)-type photochromic compound.

The base used to prepare the alkaline aqueous medium can be a conventional basic reagent, e.g., an alkali metal hydroxide such as sodium or potassium hydroxide, or an amine such as triethylamine. In the latter case, the triethylammonium hydrohalide salt is separated from the organic phase by filtration. Pre-forming of the Fischer's Base reactant has the further added advantage of eliminating the presence of base from the condensation reaction.

In accordance with an embodiment of the present invention, Fischer's Base reactant is introduced into the condensation reaction vessel in the form of a solution in a non-polar organic solvent. This solvent is chemically inert with respect to the reactants and photochromic product, and preferably has a boiling point greater than the boiling point of the azeotrope formed by water and the polar solvent used to introduce the polycyclic reactant, i.e., the oxazine- or pyran-forming reactant, and the organic polar solvent itself. Preferably, the non-polar solvent forms a triple azeotrope with co-product water and the polar solvent, e.g., ethanol. Particularly contemplated as the non-polar solvent are $C_5-C_9$ liquid hydrocarbons, e.g., the pentanes, hexanes, heptanes, octanes, and nonanes. Because of their low volatility, a vacuum is preferably used with the octanes and nonanes.

The second reactant, i.e., the polycyclic reactant represented by graphic formula V, is introduced into the reaction vessel in accordance with the present method in a liquid (at standard temperature and pressure) polar solvent. This solvent should be chemically inert with respect to the reactants and photochromic product, have a boiling point less than the non-polar hydrocarbon solvent and preferably form an azeotrope with co-product water formed during the condensation reaction, which azeotrope boils below the boiling point of the non-polar solvent. Preferably, the polar solvent is substantially water free, i.e., is an anhydrous alkanol. The reactant of graphic formula V is sparingly soluble in the polar solvent and hence, is added to the reaction vessel as a finely-divided suspension in the polar solvent, i.e., as a slurry. Polar solvents that may be used in accordance with the present method are $C_1$–$C_4$ alkanols, preferably the $C_2$ and $C_3$ alkanols, i.e., ethanol and isopropanol.

In accordance with the present invention, the Fischer's Base reactant in non-polar solvent and polycyclic reactant of graphic formula V in polar solvent are brought together in a suitable reaction vessel equipped with an agitator for thorough mixing of the reactant streams, and heated to temperatures sufficient to form the corresponding spiro(indoline)-type compound, i.e., by condensing the two reactants with the formation of co-product water. Simultaneously, co-product water is removed from the reaction medium by means of the azeotrope formed with the polar solvent. The polar and non-polar solvents are preferably miscible so that a single liquid phase is present in the reaction vessel.

Typically, condensation reaction temperatures of between about 65° C. and about 80° C. are suitable for preparing the spiro(indoline)-type photochromic compounds of graphic formula I. In a preferred embodiment, the reaction vessel is heated by means known in the art, which avoid the formation of hot spots on the wall of the reaction vessel or within the reaction medium so that substantially uniform temperatures are provided throughout the reaction medium. Avoidance of such hot spots in the reaction zone are thought to assist in reducing the formation of tarry by-products.

The amount of non-polar organic solvent used should be sufficient to solvate the Fischer's Base. The amount of non-polar solvent used is not critical beyond that required to solvate the Fischer's Base reactant and provide a liquid medium within which the condensation reaction can be performed. The amount of polar solvent used should be sufficient to provide a dilute slurry of the polycyclic reactant of formula V. The polar and non-polar solvents may be used in substantially equal volumes.

In one embodiment of the present method, the non-polar solvent containing the Fischer's Base reactant is charged to the reaction vessel and subsequently from about 10 to about 100 volume percent of the polar solvent, basis the non-polar solvent, is added thereto. The reaction medium is brought to reaction temperature and the remaining slurry of second reactant in polar solvent added slowly to the reactor at about the volumetric rate at which the water-polar solvent azeotrope is removed from the reaction vessel. In this manner, the reaction volume is maintained at a substantially constant level. Preferably, the volumetric ratio of polar to non-polar solvent in the reaction vessel is maintained at about 1:1 during the reaction.

The method of the present invention has been found to improve the yield of spiro(indoline)-type compound by at least 100 percent, e.g., from about a 25-30 percent yield to greater than 50-60 percent yield.

The present process is more particularly described in the following examples which are intended as illustrative only since numerous modifications and variations therein will be apparent to those skilled in the art.

EXAMPLE I

Into a reaction flask padded with nitrogen was charged 500 milliliters of water, 5.25 grams of solid sodium hydroxide, and 20.16 grams of an indolium iodide isomeric mixture of: 1,2,3,3,4,5-hexamethyl-indolium iodide and 1,2,3,3,5,6-hexamethyl-indolium iodide. To this aqueous media was added 200 milliliters of n-heptane and the resulting mixture stirred for about 30 minutes at room temperature, i.e., about 25° C.

The heptane phase was separated from the aqueous phase and the aqueous phase washed with an additional 200 milliliters of heptane. The heptane wash was added to the original heptane phase. The resulting mixed heptane phase (about 400 milliliters) was mixed with 100 milliliters of denatured anhydrous ethanol and the resulting reaction medium added to a two-liter reaction flask equipped with a stirrer and steam jacket. The contents of the reaction flask were heated to 70° C.

A two-liter Erlenmeyer flask containing two liters of denatured anhydrous ethanol and 11.0 grams of 5-nitroso-6-hydroxyquinoline at a temperature of about 25° C. was added slowly to the contents of the reaction flask. After about 250 milliliters of the substituted quinoline-ethanol reactant had been added, the reaction solution turned emerald green.

An additional 1 liter of denatured anhydrous ethanol was added to the substituted quinoline-ethanol mixture in the Erlenmeyer flask and the resulting slurry slowly added to the reaction vessel. The reaction temperature of the reaction vessel was maintained between about 75° and 78° C. A water-ethanol distillate was removed from the reaction vessel at about the same volumetric rate as the substituted quinoline-ethanol reactant was added to the reaction vessel.

After all of the substituted quinoline-ethanol slurry had been added to the reaction flask, the excess ethanol was distilled over and 100 milliliters of heptane added to the reaction vessel to replenish heptane carried overhead with the ethanol distillate.

The heptane was later removed by distillation. The resulting reaction mass was chilled in an ice bath and then filtered through a medium frit filter. The filter cake was washed with chilled hexane. The washed filter cake was air dried and then placed in a vacuum oven maintained at less than 40° C. for a brief period. 15.40 grams of the product 1,3,3,4 5 (or 5.6)-pentamethylspiro [indoline-2,3'-[3H]pyrido[3,2-f][1,4]benzoxazine] was obtained, which calculated to about a 71 percent yield based on the amount of 5-nitroso-6-hydroxyquinoline. Assay was confirmed by High Performance Liquid Chromatography (HPLC).

EXAMPLE II

A 2-liter steam jacketed flask fitted with addition burette, thermometer, stirrer, 12-inch Vigreaux column leading to a condenser and distillate flask was charged with 10.59 grams of solid sodium hydroxide, 500 milliliters of water, 200 milliliters of n-heptane and 40.40 grams of the indolium iodide salt described in Example I. The mixture was stirred vigorously for 30 minutes at room temperature. The aqueous phase was separated from the heptane phase and the aqueous phase washed with 100 milliliters of heptane twice. The heptane wash was added to the heptane phase together with 200 milliliters of denatured anhydrous ethanol.

A slurry of 22.0 grams of 5-nitroso-6-hydroxyquinoline in four liters of denatured ethanol was introduced to the reaction flask containing the heptane-Fischer's Base solution at about 30 milliliters per minute. While maintaining the temperature of the reaction medium in the flask at between 65° and 80° C. a water-ethanol azeotrope was removed from the reaction flask and condensed. The reaction solution was stripped of excess solvent by vacuum distillation down to a total volume of about 500 milliliters. The concentrated reaction mixture, was chilled in an ice bath (0° C.) and filtered with a coarse frit glass filter funnel. The solids retained on the frit were washed twice with about 100 milliliters each of a chilled 1:1 mixture of hexane and acetone. The product was air dried to recover 31.22 grams of product of about 98.0 percent purity, which calculated to a 71.9 percent yield based on the 5-nitroso-6-hydroxyquinoline. Assay was confirmed by HPLC.

EXAMPLE III

Into a three-necked round bottom flask padded with nitrogen was added 1.67 grams (41.8 millimoles) of sodium hydroxide dissolved in 30 milliliters of water. To this sodium hydroxide solution was added 8.61 grams (26.2 millimoles) of an isomeric mixture of 1,2,3,3,4,5 (and 5,6)-hexamethyl-indolium iodide with stirring. After 5 minutes, 30 milliliters of n-heptane was added to the round bottom flask with continued vigorous stirring. After about 1 hour, the mixture was poured into a separatory funnel and the phases separated. The aqueous phase was washed with 10 milliliters of n-heptane and the n-heptane wash combined with the organic layer in the separatory funnel. This mixture was added to a 3-necked round bottom flask equipped with magnetic stirrer, Dean-stark trap and condenser and pressure equalizing addition funnel. 20 milliliters of absolute ethanol were added to the reaction flask and the contents heated to reflux.

A slurry of 5.32 grams (26.2 millimoles) of 3-methoxy-5-nitroso-6-hydroxynaphthalene and 75 milliliters of denatured absolute ethanol was prepared and a portion added to the addition funnel. The slurry was added dropwise to the reaction flask while simultaneously removing distillate by means of the Dean-stark trap. The temperature of the reaction flask was maintained between about 72° C. and 78° C. during addition of the slurry. Additional ethanol was added to the ethanol-substituted naphthalene reaction mixture, as required, to maintain a dilute slurry. Approximately 3 and ¾ hours were required to add all of the substituted naphthalene reactant to the reaction flask. The reaction mixture was warmed at 76° C. for an additional 45 minutes.

At the end of the reaction, the solvent in the reaction flask was reduced to about 50 milliliters and the reaction mass cooled to room temperature and then cooled in an ice bath. The cooled reaction mass was transferred to a medium porosity frit filter and the solvent removed gently. The filter cake was washed 3 times with about 3 to 4 milliliters of cold hexane and twice with about 3 to 4 milliliters of cold acetone. The washed filter cake was dried in air to a constant weight. 6.73 grams of 9'-methoxy-1,3,3,4,5(or 5,6)-pentamethylspiro[indoline-2,3'-[3H]-naphtho[2,1-b]-1,4-oxazine] were recovered which amounts to a 67 percent yield. The structure of the recovered product was confirmed by proton Nuclear Magnetic Resonance (NMR) and assay by High Performance Liquid Chromatography (HPLC) analyses.

Although the present invention has been described with reference to specific details of certain embodiments thereof, it is not intended that such details should be regarded as limitations upon the scope of the invention except as and to the extent that they are included in the accompanying claims.

What is claimed is:

1. A process for preparing spiro (indoline)-type compounds represented by the following graphic formula,

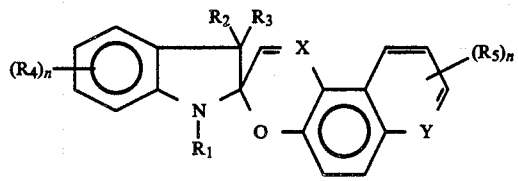

wherein $R_1$ is selected from the group consisting of hydrogen, $C_1$–$C_8$ alkyl, phenyl, phen ($C_1$–$C_4$)alkyl, allyl and mono- and di-substituted phenyl, said phenyl substituents being selected from $C_1$–$C_4$ alkyl and $C_1$–$C_5$ alkoxy; $R_2$ and $R_3$ are each selected from the group consisting of hydrogen, $C_1$–$C_5$ alkyl, phenyl, mono- and di-substituted phenyl, benzyl or combine to form a cyclic ring selected from the group consisting of a $C_6$–$C_8$ alicyclic ring, norbornyl and adamentyl, said phenyl substituents being selected from the group consisting of $C_1$–$C_4$ alkyl and $C_1$–$C_5$ alkoxy; $R_4$ is selected from the group consisting of $C_1$–$C_5$ alkyl, halogen, $C_1$–$C_5$ alkoxy, nitro, cyano, $C_1$–$C_4$ haloalkyl, $C_1$–$C_4$ polyhaloalkyl, and $C_1$–$C_8$ alkoxy carbonyl; $R_5$ is selected from the group consisting of halogen and $C_1$–$C_4$ alkoxy; X and Y are each selected from the group consisting of carbon and nitrogen; and n is 0, 1 or 2, which comprises mixing:

(a) a solution of Fischer's Base in non-polar organic solvent, said reactant being represented by the following graphic formula,

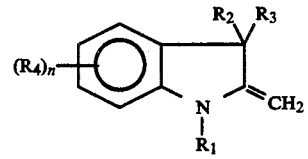

wherein $R_1$, $R_2$, $R_3$, $R_4$ and n are as defined herein, and (b) a slurry of a second reactant in polar organic solvent, said second reactant being represented by the following graphic formula,

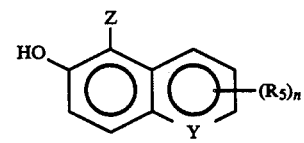

wherein $R_5$, Y, and n are as defined above and Z is nitroso or formyl, in a reaction vessel at temperatures sufficient to cause condensation of the aforesaid reactants, while removing co-product water, said non-polar organic solvent and polar organic solvent being miscible.

2. The process of claim 1, wherein co-product water is removed from the reaction vessel, as a water-polar solvent azeotrope.

3. The process of claim 2, wherein the non-polar solvent has a boiling point greater than the polar solvent and water-polar solvent azeotrope.

4. The process of claim 1, wherein the non-polar solvent is a $C_5$–$C_9$ liquid hydrocarbon.

5. The process of claim 2, wherein the polar solvent has a boiling point less than the non-polar solvent, and forms an azeotrope with co-product water, which azeotrope has a boiling point below the boiling point of the non-polar solvent.

6. The process of claim 1, wherein the polar solvent is a $C_1$–$C_4$ alkanol.

7. The process of claim 6, wherein the polar solvent is substantially water-free.

8. The process of claim 1, wherein condensation temperatures are from about 65° C. to about 80° C.

9. The process of claim 1, wherein the reactants are heated in the reaction vessel in a manner that avoids hot spots on the reaction vessel wall.

10. The process of claim 1, wherein the volumetric ratio of polar to non-polar solvent in the reaction vessel is about 1:1.

11. The process of claim 1, wherein the slurry of second reactant is added to the solution of Fischer's Base in the reaction vessel at rate such that the reaction volume remains substantially constant during said addition.

12. The process of claim 2, wherein co-product water is removed from the reaction vessel as a water-polar solvent-non-polar solvent triple azeotrope.

13. The process of claim 1, wherein the Fischer's Base reactant is formed in the reaction vessel in situ by reaction of the corresponding indolium salt and a basic reagent.

14. The process of claim 2, wherein $R_1$ is hydrogen, $C_1$–$C_4$ alkyl, phenyl or benzyl; $R_2$ and $R_3$ are each $C_1$–$C_5$ alkyl; $R_4$ is $C_1$–$C_2$ alkyl, chlorine, bromine, $C_1$–$C_5$ alkoxy; $C_1$–$C_4$ haloalkyl or $C_1$–$C_4$ polyhaloalkyl; and $R_5$ is chlorine, bromine, hydrogen or $C_1$–$C_4$ alkoxy.

15. The process of claim 14, wherein from 10 to 100 volume percent of polar solvent, basis the non-polar solvent, is charged to the reaction vessel containing the Fischer's Base non-polar solvent reactant solution; the resulting mixture is heated to condensation temperatures; and the slurry of second reactant in polar solvent added slowly to the reaction vessel.

16. The process of claim 14, wherein the non-polar solvent is a $C_5$–$C_9$ liquid hydrocarbon, the polar solvent is a $C_1$–$C_4$ alkanol, the non-polar solvent having a boiling point greater than the polar solvent and the water-polar solvent azeotrope.

17. The process of claim 16, wherein condensation temperatures are from about 65° C. to about 80° C.

18. The process of claim 15, wherein the non-polar solvent is a $C_5$–$C_9$ liquid hydrocarbon, the polar solvent is a $C_1$–$C_4$ alkanol, the non-polar solvent having a boiling point greater than the polar solvent and the water-polar solvent azeotrope.

* * * * *